(12) United States Patent
Frost et al.

(10) Patent No.: US 7,718,428 B2
(45) Date of Patent: May 18, 2010

(54) MYELOID COLONY STIMULATING FACTOR AND USES THEREOF

(75) Inventors: Gregory I. Frost, Solana Beach, CA (US); Per Borgstrom, La Jolla, CA (US)

(73) Assignee: Halozyme, Inc., San Diego, CA (US)

( * ) Notice: Subject to any disclaimer, the term of this patent is extended or adjusted under 35 U.S.C. 154(b) by 694 days.

(21) Appl. No.: 11/431,181

(22) Filed: May 9, 2006

(65) Prior Publication Data

US 2006/0247201 A1 Nov. 2, 2006

Related U.S. Application Data

(62) Division of application No. 10/182,088, filed as application No. PCT/US01/02575 on Jan. 25, 2001, now abandoned.

(60) Provisional application No. 60/177,913, filed on Jan. 25, 2000.

(51) Int. Cl.
- *A01N 1/02* (2006.01)
- *A61K 38/00* (2006.01)
- *A61K 38/43* (2006.01)
- *C07K 14/00* (2006.01)

(52) U.S. Cl. .......................... 435/375; 435/2; 424/94.1; 514/2; 530/350

(58) Field of Classification Search .................. None
See application file for complete search history.

(56) References Cited

U.S. PATENT DOCUMENTS

| 6,103,525 A * | 8/2000 | Stern et al. .................. 435/326 |
| 6,123,938 A * | 9/2000 | Stern et al. ............... 424/94.62 |

FOREIGN PATENT DOCUMENTS

| JP | 8-20599 A | 1/1996 |
| WO | WO 98/16655 | * 4/1998 |
| WO | WO 99/29841 A1 | 6/1999 |

OTHER PUBLICATIONS

Smith et al., J. Am. Acad. Dermatol., 1997, vol. 36:239-242.*
Treacy et al., Br. J. Haematol., 1987, vol. 65(3):289-294.*
Csóka et al., "Expression Analysis of Six Paralogous Human Hyaluronidase Genes Clustered on Chromosomes 3p21 and 7q31", *Genomics*, 60:356-361 (1999).
Fixe et al., "M-CSF: Haematopoietic Growth Factor or Inflammatory Cytokine?", *Cytokine*, 10(1):32-37 (1998).
Frost et al., "Purification, Cloning, and Expression of Human Plasma Hyaluronidase", *Biochemical & Biophysical Research Communications*, 236:10-15 (NCBI Accession No. U96078) (1997).
Kikuchi et al., "DNA Coding Protein Having Ability to Proliferate and Differentiate Thymus Macrophage-Based Cell and Cerebral Microglia Cell", NCBI Accession No. E13938.
Menzel et al., "Hyaluronidase and Its Substrate Hyaluronan: Biochemistry, Biological Activities and Therapeutic Uses", *Cancer Letters*, 131:3-11 (1998).
Natowicz et al., "Clinical and Biochemical Manifestations of Hyaluronidase Deficiency", *The New England Journal of Medicine*, 335(14):1029-1033 (1996).
Root & Dale, "Granulocyte Colony-Stimulating Factor and Granulocyte-Macrophage Colony-Stimulating Factor: Comparisons and Potential for Use in the Treatment of Infections in Nonneutropenic Patients", *The Journal of Infectious Disease*, 179(Suppl. 2):S342-S352 (1999).
Triggs-Raine et al., "Mutations in *HYAL1*, a Member of a Tandemly Distributed Multigene Family Encoding Disparate Hyaluronidase Activities, Cause a Newly Described Lysosomal Disorder, Mucopolysaccharidosis IX", *Proc Natl Acad Sci USA.*, 96:6296-6300 (1999).

* cited by examiner

*Primary Examiner*—Gary B Nickol
*Assistant Examiner*—Xiaozhen Xie
(74) *Attorney, Agent, or Firm*—DLA Piper LLP (US)

(57) ABSTRACT

The identification of the HYAL1 hyaluronidase enzyme as a human plasma-derived myeloid colony-stimulating factor (CSF), designated CSF5-hyaluronidase, its recombinant production and methods of use are described. This protein may be used for the treatment of myelosuppression as may occur after irradiation, chemotherapy or other diseases where an increase in leukocyte levels may be beneficial. For example, CSF5-hyaluronidase may be used to enhance the immune response to viral infection or other diseases associated with immune suppression.

3 Claims, No Drawings

SEQUENCE LISTING

<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
<223> OTHER INFORMATION: PCR primer

<400> SEQUENCE: 1
atcgaagaca ctgacatcca cgtccacacc                                      30

<210> SEQ ID NO 2
<211> LENGTH: 23
<212> TYPE: DNA
<213> ORGANISM: Artificial Sequence
<220> FEATURE:
<223> OTHER INFORMATION: PCR primer

<400> SEQUENCE: 2
actcactata gggctcgagc ggc                                             23

<210> SEQ ID NO 3
<211> LENGTH: 29
<212> TYPE: DNA
<213> ORGANISM: Artificial Sequence
<220> FEATURE:
<223> OTHER INFORMATION: PCR primer

<400> SEQUENCE: 3
tgcctctcca ggcaccactg ggtgtttgc                                       29

<210> SEQ ID NO 4
<211> LENGTH: 18
<212> TYPE: DNA
<213> ORGANISM: Artificial Sequence
<220> FEATURE:
<223> OTHER INFORMATION: PCR primer

<400> SEQUENCE: 4
gtgccatggc agcccacc                                                   18

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
atcaccacat gctcttccgc                                                 20

<210> SEQ ID NO 6
<211> LENGTH: 19
<212> TYPE: DNA
<213> ORGANISM: Artificial Sequence
<220> FEATURE:
<223> OTHER INFORMATION: PCR primer

<400> SEQUENCE: 6
aggttgtcct cgaccagtc                                                  19

<210> SEQ ID NO 7
<211> LENGTH: 21

```
<212> TYPE: DNA
<213> ORGANISM: Artificial Sequence
<220> FEATURE:
<223> OTHER INFORMATION: PCR primer

<400> SEQUENCE: 7
atgtgcaact cagtgtgtgg c                                               21

<210> SEQ ID NO 8
<211> LENGTH: 2517
<212> TYPE: DNA
<213> ORGANISM: Homo sapiens
<220> FEATURE:
<221> NAME/KEY: CDS
<222> LOCATION: (617)...(1921)

<400> SEQUENCE: 8
ttcctccagg agtctctggt gcagctgggg tggaatctgg ccaggccctg cttaggcccc     60
catcctgggg tcaggaaatt tggaggataa ggcccttcag ccccaaggtc agcagggacg    120
agcgggcaga ctggcgggtg tacaggaggg ctgggttgac ctgtccttgg tcactgaggc    180
cattggatct tcctccagtg gctgccagga tttctggtgg aagagacagg aaggcctccc    240 cccccttggtc gggtcagcct gggggctgag ggcctggctg tcagccactc ttcccagaac    300
atatgtcatg gcctcagtgg ctcatgggga agcaggggtg ggcgagctta ggctagagca    360
agtcctgtgg gagatggcag aggcctggtc tgagaggcaa ctcggatgtg ccctccagtg    420
gccatgctcc cctccatgcg tctccctgc cctcctggag ccctgcaggt caatgtttaa    480
cagaaaccag agcagcggtg gattaatgcg caagggctca gcccccagc cctgagcagt    540 gggggaatcg gagactttgc aacctgttct cagctctgcc tccctggcc aggttgtcct    600 cgaccagtcc cgtgcc atg gca gcc cac ctg ctt ccc atc tgc gcc ctc ttc    652
               Met Ala Ala His Leu Leu Pro Ile Cys Ala Leu Phe
               1               5                   10 ctg acc tta ctc gat atg gcc caa ggc ttt agg ggc ccc ttg cta ccc       700
Leu Thr Leu Leu Asp Met Ala Gln Gly Phe Arg Gly Pro Leu Leu Pro
        15                  20                  25 aac cgg ccc ttc acc acc gtc tgg aat gca aac acc cag tgg tgc ctg       748
Asn Arg Pro Phe Thr Thr Val Trp Asn Ala Asn Thr Gln Trp Cys Leu
    30                  35                  40 gag agg cac ggt gtg gac gtg gat gtc agt gtc ttc gat gtg gta gcc       796
Glu Arg His Gly Val Asp Val Asp Val Ser Val Phe Asp Val Val Ala
45                  50                  55                  60 aac cca ggg cag acc ttc cgc ggc cct gac atg aca att ttc tat agc       844
Asn Pro Gly Gln Thr Phe Arg Gly Pro Asp Met Thr Ile Phe Tyr Ser
                65                  70                  75 tcc cag ctg ggc acc tac ccc tac tac acg ccc act ggg gag cct gtg       892
Ser Gln Leu Gly Thr Tyr Pro Tyr Tyr Thr Pro Thr Gly Glu Pro Val
            80                  85                  90 ttt ggt ggt ctg ccc cag aat gcc agc ctg att gcc cac ctg gcc cgc       940
Phe Gly Gly Leu Pro Gln Asn Ala Ser Leu Ile Ala His Leu Ala Arg
        95                  100                 105 aca ttc cag gac atc ctg gct gcc ata cct gct cct gac ttc tca ggg       988
Thr Phe Gln Asp Ile Leu Ala Ala Ile Pro Ala Pro Asp Phe Ser Gly
    110                 115                 120 ctg gca gtc atc gac tgg gag gca tgg cgc cca cgc tgg gcc ttc aac      1036
Leu Ala Val Ile Asp Trp Glu Ala Trp Arg Pro Arg Trp Ala Phe Asn
125                 130                 135                 140 tgg gac acc aag gac att tac cgg cag cgc tca cgg gca ctg gta cag      1084
Trp Asp Thr Lys Asp Ile Tyr Arg Gln Arg Ser Arg Ala Leu Val Gln
                145                 150                 155
```

```
gca cag cac cct gat tgg cca gct cct cag gtg gag gca gta gcc cag    1132
Ala Gln His Pro Asp Trp Pro Ala Pro Gln Val Glu Ala Val Ala Gln
        160             165                 170 gac cag ttc cag gga gct gca cgg gcc tgg atg gca ggc acc ctc cag    1180
Asp Gln Phe Gln Gly Ala Ala Arg Ala Trp Met Ala Gly Thr Leu Gln
        175             180                 185 ctg ggg cgg gca ctg cgt cct cgc ggc ctc tgg ggc ttc tat ggc ttc    1228
Leu Gly Arg Ala Leu Arg Pro Arg Gly Leu Trp Gly Phe Tyr Gly Phe
        190             195                 200 cct gac tgc tac aac tat gac ttt cta agc ccc aac tac acc ggc cag    1276
Pro Asp Cys Tyr Asn Tyr Asp Phe Leu Ser Pro Asn Tyr Thr Gly Gln
205             210             215                 220 tgc cca tca ggc atc cgt gcc caa aat gac cag cta ggg tgg ctg tgg    1324
Cys Pro Ser Gly Ile Arg Ala Gln Asn Asp Gln Leu Gly Trp Leu Trp
                225             230                 235 ggc cag agc cgt gcc ctc tat ccc agc atc tac atg ccc gca gtg ctg    1372
Gly Gln Ser Arg Ala Leu Tyr Pro Ser Ile Tyr Met Pro Ala Val Leu
                240             245                 250 gag ggc aca ggg aag tca cag atg tat gtg caa cac cgt gtg gcc gag    1420
Glu Gly Thr Gly Lys Ser Gln Met Tyr Val Gln His Arg Val Ala Glu
            255             260                 265 gca ttc cgt gtg gct gtg gct gct ggt gac ccc aat ctg ccg gtg ctg    1468
Ala Phe Arg Val Ala Val Ala Ala Gly Asp Pro Asn Leu Pro Val Leu
        270             275                 280 ccc tat gtc cag atc ttc tat gac acg aca aac cac ttt ctg ccc ctg    1516
Pro Tyr Val Gln Ile Phe Tyr Asp Thr Thr Asn His Phe Leu Pro Leu
285             290             295                 300 gat gag ctg gag cac agc ctg ggg gag agt gcg gcc cag ggg gca gct    1564
Asp Glu Leu Glu His Ser Leu Gly Glu Ser Ala Ala Gln Gly Ala Ala
                305             310                 315 gga gtg gtg ctc tgg gtg agc tgg gaa aat aca aga acc aag gaa tca    1612
Gly Val Val Leu Trp Val Ser Trp Glu Asn Thr Arg Thr Lys Glu Ser
                320             325                 330 tgt cag gcc atc aag gag tat atg gac act aca ctg ggg ccc ttc atc    1660
Cys Gln Ala Ile Lys Glu Tyr Met Asp Thr Thr Leu Gly Pro Phe Ile
            335             340                 345 ctg aac gtg acc agt ggg gcc ctt ctc tgc agt caa gcc ctg tgc tcc    1708
Leu Asn Val Thr Ser Gly Ala Leu Leu Cys Ser Gln Ala Leu Cys Ser
        350             355                 360 ggc cat ggc cgc tgt gtc cgc cgc acc agc cac ccc aaa gcc ctc ctc    1756
Gly His Gly Arg Cys Val Arg Arg Thr Ser His Pro Lys Ala Leu Leu
365             370             375                 380 ctc ctt aac cct gcc agt ttc tcc atc cag ctc acg cct ggt ggt ggg    1804
Leu Leu Asn Pro Ala Ser Phe Ser Ile Gln Leu Thr Pro Gly Gly Gly
                385             390                 395 ccc ctg agc ctg cgg ggt gcc ctc tca ctt gaa gat cag gca cag atg    1852
Pro Leu Ser Leu Arg Gly Ala Leu Ser Leu Glu Asp Gln Ala Gln Met
            400             405                 410 gct gtg gag ttc aaa tgt cga tgc tac cct ggc tgg cag gca ccg tgg    1900
Ala Val Glu Phe Lys Cys Arg Cys Tyr Pro Gly Trp Gln Ala Pro Trp
        415             420                 425 tgt gag cgg aag agc atg tgg tgattggcca cacactgagt tgcacatatt       1951
Cys Glu Arg Lys Ser Met Trp
430             435 gagaaccvtaa tgcactctgg gtctggccag ggcttcctca aatacatgca cagtcataca  2011
agtcatggtc acagtaaaga gtacactcag ccactgtcac aggcatattc cctgcacaca  2071
catgcatact tacagactgg aatagtggca taaggagtta gaaccacagc agacaccatt  2131
```

```
cattccatgt ccatatgcat ctacttggca aggtcataga caattcctcc agagacactg    2191
agccagtctt tgaactgcag caatcacaaa ggctgacatt cactgagtgc ctactctttg    2251
ccaatccccg tgctaagcgt tttatgtgga cttattcatt cctcacaatg aggctatgag    2311
gaaactgagt cactcacatt gagagtaagc acgttgccca aggttgcaca gcaagaaaag    2371
ggagaagttg agattcaaac ccaggctgtc tagctccggg ggtacagccc ttgcactcct    2431
actgagtttg tggtaaccag ccctgcacga cccctgaatc tgctgagagg caccagtcca    2491
gcaaataaag cagtcatgat ttactt                                        2517
```

<210> SEQ ID NO 9
<211> LENGTH: 435
<212> TYPE: PRT
<213> ORGANISM: Homo sapiens

<400> SEQUENCE: 9

```
Met Ala Ala His Leu Leu Pro Ile Cys Ala Leu Phe Leu Thr Leu Leu
 1               5                  10                  15

Asp Met Ala Gln Gly Phe Arg Gly Pro Leu Leu Pro Asn Arg Pro Phe
            20                  25                  30

Thr Thr Val Trp Asn Ala Asn Thr Gln Trp Cys Leu Glu Arg His Gly
        35                  40                  45

Val Asp Val Asp Val Ser Val Phe Asp Val Val Ala Asn Pro Gly Gln
    50                  55                  60

Thr Phe Arg Gly Pro Asp Met Thr Ile Phe Tyr Ser Ser Gln Leu Gly
65                  70                  75                  80

Thr Tyr Pro Tyr Tyr Thr Pro Thr Gly Glu Pro Val Phe Gly Gly Leu
                85                  90                  95

Pro Gln Asn Ala Ser Leu Ile Ala His Leu Ala Arg Thr Phe Gln Asp
            100                 105                 110

Ile Leu Ala Ala Ile Pro Ala Pro Asp Phe Ser Gly Leu Ala Val Ile
        115                 120                 125

Asp Trp Glu Ala Trp Arg Pro Arg Trp Ala Phe Asn Trp Asp Thr Lys
    130                 135                 140

Asp Ile Tyr Arg Gln Arg Ser Arg Ala Leu Val Gln Ala Gln His Pro
145                 150                 155                 160

Asp Trp Pro Ala Pro Gln Val Glu Ala Val Ala Gln Asp Gln Phe Gln
                165                 170                 175

Gly Ala Ala Arg Ala Trp Met Ala Gly Thr Leu Gln Leu Gly Arg Ala
            180                 185                 190

Leu Arg Pro Arg Gly Leu Trp Gly Phe Tyr Gly Phe Pro Asp Cys Tyr
        195                 200                 205

Asn Tyr Asp Phe Leu Ser Pro Asn Tyr Thr Gly Gln Cys Pro Ser Gly
    210                 215                 220

Ile Arg Ala Gln Asn Asp Gln Leu Gly Trp Leu Trp Gly Gln Ser Arg
225                 230                 235                 240

Ala Leu Tyr Pro Ser Ile Tyr Met Pro Ala Val Leu Glu Gly Thr Gly
                245                 250                 255

Lys Ser Gln Met Tyr Val Gln His Arg Val Ala Glu Ala Phe Arg Val
            260                 265                 270

Ala Val Ala Ala Gly Asp Pro Asn Leu Pro Val Leu Pro Tyr Val Gln
        275                 280                 285

Ile Phe Tyr Asp Thr Thr Asn His Phe Leu Pro Leu Asp Glu Leu Glu
    290                 295                 300
```

-continued

```
His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ala Ile
                325                 330                 335

Lys Glu Tyr Met Asp Thr Thr Leu Gly Pro Phe Ile Leu Asn Val Thr
            340                 345                 350

Ser Gly Ala Leu Leu Cys Ser Gln Ala Leu Cys Ser Gly His Gly Arg
        355                 360                 365

Cys Val Arg Arg Thr Ser His Pro Lys Ala Leu Leu Leu Leu Asn Pro
    370                 375                 380

Ala Ser Phe Ser Ile Gln Leu Thr Pro Gly Gly Gly Pro Leu Ser Leu
385                 390                 395                 400

Arg Gly Ala Leu Ser Leu Glu Asp Gln Ala Gln Met Ala Val Glu Phe
                405                 410                 415

Lys Cys Arg Cys Tyr Pro Gly Trp Gln Ala Pro Trp Cys Glu Arg Lys
            420                 425                 430

Ser Met Trp
        435

<210> SEQ ID NO 10
<211> LENGTH: 8
<212> TYPE: PRT
<213> ORGANISM: Homo sapiens

<400> SEQUENCE: 10

Phe Arg Gly Pro Leu Leu Val Pro
1               5
```

MYELOID COLONY STIMULATING FACTOR AND USES THEREOF

CROSS REFERENCE TO RELATED APPLICATION(S)

This application is a divisional of U.S. application Ser. No. 10/182,088, filed Nov. 26, 2002, now abandoned, which is an application filed under 35 U.S.C. §371 National Stage application of PCT Application No. PCT/US2001/02575 filed Jan. 25, 2001, which claims the benefit under 35 U.S.C. § 119(e) to U.S. application Ser. No. 60/177,913 filed Jan. 25, 2000, now abandoned. The disclosure of each of the prior applications is considered part of and is incorporated by reference in the disclosure of this application.

FIELD OF THE INVENTION

The present invention relates to the discovery that the previously-reported human hyaluronidase, HYAL1, is actually a new member of a class of molecules known collectively as myeloid colony stimulating factors.

BACKGROUND THE INVENTION

Colony stimulating factors are proteins capable of influencing the growth and differentiation of cells responsible for the cellular components of blood in the body. Colony Stimulating factors have traditionally been defined by their ability to stimulate growth of colonies of bone marrow cells in semisolid media. Macrophage colony stimulating factors are a subclass of colony stimulating factors that play a role in the regulation of immune responses by potentiating the proliferation and differentiation of macrophages from immature hematopoietic progenitor cells, and inducing effector functions of mature macrophages including secretion of interferon-.gamma, tumor necrosis factor and non-M-CSF colony stimulating activities.

The ability of certain factors produced in very low concentration in a variety of tissues to stimulate the growth and development of bone marrow progenitor cells into granulocytes and/or macrophages has been known for many years. The presence of such factors in sera, urine samples, and tissue extracts from a number of species is demonstrable using assays which measure the stimulation of colony formation by bone marrow cells plated in semi-solid culture medium. There is no known in vivo assay. As these factors induce the formation of such colonies, the factors collectively have been called Colony Stimulating Factors (CSF).

Colony Stimulating Factors have been purified from a number of tissue sources and species. Japanese Pat. No. 8,020,599 teaches of a rat myoid cell derived colony-stimulating factor capable of stimulating rat thymic macrophages and migroglia cells. Some colony stimulating factors are species restricted in their activity, such that CSF's derived from one species may lack colony forming activity in distantly related species (Shanafelt et al J Biol Chem 1991 Jul. 25; 266(21): 13804-10).

It has been shown that there are at least three subclasses of human CSF proteins defined according to the types of cells found in the resultant colonies. One subclass, CSF-1 results in colonies containing predominantly macrophages. Other subclasses produce colonies of both neutrophilic granulocytes and macrophages; which contain exclusively neutrophilic granulocytes; and which contain neutrophilic and eosinophilic granulocytes and macrophages.

Treatment of patients suffering from AIDS with colony stimulating factors, alone or together with erythropoietin and/or an antiviral agent and/or IL-2, is reported in PCT W087/03204 and U.S. Pat. No. 4,482,485. These references teach that CSF can be used for a supporting role in the treatment of cancer. In addition, EP 118,915 reports production of CSF for preventing and treating granulocytopenia and macrophagocytopenia in patients receiving cancer therapy, for preventing infections, and for treating patients with implanted bone marrow. In addition, CSFs stimulate nonspecific tumoricidal activity (Ralph et al, *Immunobiol* 172:194-204, 1986). CSF has no immediate direct role in activation of macrophages for tumoricidal and microbiocidal activities against fibrosarcoma 1023, lymphoma 18-8, and *L. tropica* amastigotes (Ralph et al., 76:10-21, 1983). The combination of CSF-1 and lymphokine has an added tumoricidal effect on murine sarcoma TU5 targets (Ralph et al., *Cell. Immunol.* 105:270-279, 1987). Warren et al. (*J Immunol.* 137:2281-2285, 1986) disclose that CSFs stimulate monocyte production of interferon, TNF and colony stimulating activity. Lee et al. (*J. Immunol.* 138:3019-3022, 1987) disclose CSF-induced resistance to viral infection in murine macrophages.

SUMMARY OF THE INVENTION

The present invention is based on the discovery that the human protein HYAL1, with previously reported hyaluronidase activity, has potent colony-stimulating activity. For this reason, this molecule is renamed herein as CSF5-hyaluronidase.

One embodiment of the invention is a process for purifying human CSF5-hyaluronidase protein comprising subjecting a biological sample of human or human tissue origin to the steps of phase extraction, cation exchange chromatography and hydroxyapatite chromatography, such that purified human CSF5-hyaluronidase is recovered.

The invention also includes a method for increasing the number of myeloid progenitors in a cell population, comprising the step of contacting the cell population with an exogenously-derived CSF5-hyaluronidase.

The invention further provides a method for treating a mammal with a myelosuppressed condition, comprising the step of administering to a mammal an effective amount of exogenously-derived CSF5-hyaluronidase. In one embodiment, CSF5-hyaluronidase is administered in conjunction with a treatment selected from the group consisting of surgery, radiation therapy and chemotherapy. In certain embodiments, the myelosuppression is associated with radiation, chemotherapy or viral infection.

The invention further includes a method for treating a mammal with a myelosuppressed condition, comprising the step of administering to said mammal nucleic acid operatively encoding CSF5-hyaluronidase such that SCF5-hyaluronidase is expressed in said mammal. The nucleic acid may advantageously be in an expression vector, preferably operatively linked to a promoter, which may be, for example, an exogenous promoter, an inducible promoter, a viral promoter, a constitutive promoter, or a heterologous human promoter.

A further aspect of the present invention is a method for enhancing the production of cytokines by myeloid cells, comprising the step of contacting said myeloid cells with exogenously-derived CSF5-hyaluronidase. Cytokines contemplated in the present invention include, for example, interferon, interleukin, tumor necrosis factor and myeloid colony stimulating factor.

DETAILED DESCRIPTION OF THE INVENTION

The present invention relates to the discovery of colony-stimulating activity associated with a protein known in the literature as HYAL1. This protein represents a new member of the colony stimulating factor family of the monocytic subclass, and has a unique dual function in that the biochemically purified and recombinant protein also possesses glycosaminoglycan degrading activity towards chondroitin sulfates and hyaluronan under acidic conditions. This protein, previously known as HYAL1, has been recently purified, cloned and sequenced by virtue of its glycosaminoglycan degrading, or hyaluronidase activity (Frost et al, *Biochem. Biophys. Res. commun.* 236:5-10, 1997). Six paralogous sequences to HYAL1 have been identified in the human genome (Csoka et al, Genomics 1999 Sep. 15; 60(3):356-61). Hyaluronidase like genes have been identified in other mammalian species, including mouse and rat (Strobl et al, Genomics 1998 Oct. 15; 53 (2):214-9) (Genbank Accession Number 4104235). The orthologous relationship between such genes has not been established in some species.

Prior to the present invention, no myelostimulative or colony stimulating activity had been attributed to this glycosaminoglycandegrading enzyme. The HYAL1 enzyme has high specificity and is present predominantly in human plasma at a concentration of 20-50 µg/ml (Frost et al, 1997/. Because of its CSF activity, the HYAL1 gene product should be redefined as CSF5-hyaluronidase.

Human CSF5-hyaluronidase supports monocyte proliferation and/or differentiation in vitro. This novel property of the gene product was identified from the treatment of human peripheral blood monocytes in vitro with recombinant CSF5-hyaluronidase produced as described in the examples below. Based on this discovery, CSF5-hyaluronidase and vectors encoding this protein are suitable for use in supporting hematopoiesis in vivo, and in treating immune deficiencies associated with chemotherapy or viral infection.

CSF5-hyaluronidase is also used in the present invention to increase the number of monocytes in a cell population by contacting the cell population with an effective amount of the protein. This effective amount is, in general, between about 0.01 µg/ml and 100 mg/ml, preferably between about 0.1 µg/ml and 10 mg/ml, and more preferably between about 1 ng/ml and 1 mg/ml. These amounts can be optimized for any cell population using standard dose-response curves. This is useful for producing large numbers of cultured monocytes which can be used therapeutically or for screening assays to discover compounds capable of stimulating release of cytokines from monocytes. It can also be used in vivo to treat myeloid-cell insufficiency.

Note that referred embodiments of the present invention utilize exogenously-derived CSF5-hyaluronidase. "Exogenously-derived," in the context of treatment of a cell population or a mammal, is defined as CSF5-hyaluronidase that has been introduced into a system, such as recombinantly-produced CSF5-hyaluronidase, purified or isolated CSF5-hyaluronidase, CSF5-hyaluronidase produced from another organism, or CSF5-hyaluronidase previously purified from tissues or fluids of the same organism, at a different point in time. CSF5-hyaluronidase produced by exogenously-introduced polynucleotide encoding that protein is also defined as "exogenously-derived" for purposes of the present invention.

Although various methods of treatment of cell populations and mammals (including human and non-human mammals) are described herein, it will be appreciated that the present invention also contemplates use of CSF5-hyaluronidase (or polynucleotide encoding CSF5-hyaluronidase) in the preparation of a medicament for the practice of each and every treatment method described herein. Such medicaments are typically prepared by formulating the CSF5-hyaluronidase with a pharmaceutically-acceptable carrier, of well-known type. Such carriers are typically injectable carriers, although inhalable formulations and other methods of protein delivery are also contemplated.

In one aspect, the invention relates to methods of enhancing production of cytokines by monocytes, particularly interferon, tumor necrosis factor and myeloid CSF, by treating the monocytes with an effective amount of CSF5-, either native or recombinant. In another aspect, the invention relates to methods of enhancing the killing of target cells by macrophages, of enhancing the production of white blood cells from stem cells or enhancing the immune system of a subject, of inducing resistance to viral infections in macrophages, of promoting wound healing, and of treating tumor cells by using an effective tumor-treating amount of CSF5-hyaluronidase of the present invention. In addition, the invention relates to pharmaceutical and therapeutic compositions comprising CSF5-hyaluronidase, and to a mixture thereof with an excipient or a cytokine or lymphokine.

In another embodiment of the present invention, there are provided methods for the stimulation of cells of the monocytic lineage by way of gene transfer of CSF5-hyaluronidase encoding nucleic acids. As will be appreciated by those of skill in the art, there are numerous methods available to express a gene, all of which are contemplated for use in accordance with the present invention. In a particular aspect of the present invention, CSF5-hyaluronidase gene expression is accomplished by introduction of the cDNA encoding the CSF5-hyaluronidase in a gene construct (See, e.g., SEQ ID NO: 8 for the sequence of human CSF5 hyaluronidase mRIMA). Expression of CSF5 by way of virus-mediated transfer (e.g. retroviruses, adenoviruses), naked nucleic acids and other means known by those skilled in the art are available methods to transfer the CSF5-hyaluronidase gene into a patient. Gene delivery systems are described by Feigner et al. (*Hum. Gene Ther.* 8:511-512, 1997) and include cationic lipid-based delivery systems (lipoplex), polycation-based delivery systems (polyplex) and a combination thereof (lipopolyplex), all of which are contemplated for use in the present invention.

Host-vector systems for the expression of CSF5-hyaluronidase may be prokaryotic or eukaryotic, although eukaryotic expression vectors are preferred. Many such expression vectors are known and commercially available. Standard techniques for the construction of these expression vectors are well known and can be found in references such as Sambrook et al., or in any of the widely available laboratory manuals on recombinant DNA technology. Expression may be accomplished, for example, by transforming prokaryotic or eukaryotic cells with a suitable vector encoding CSF5-hyaluronidase. The DNA sequence can be expressed directly in mammalian cells under the control of a suitable promoter. Heterologous promoters well-known by those skilled in the art can be used. Examples of such promoters include the human cytomegalovirus (CMV) promoter, the SV40 promoter, the herpes simplex virus (HSV) thymidine kinase (TK) gene promoter, the adenovirus immediate early gene promoter and retroviral long terminal repeats. The use of constitutive, inducible and tissue-specific promoters are all within the scope of the present invention. The expression vector also typically contains a selectable marker, such as antibiotic resistance, to select for cells which are expressing the protein. Other nucleotide sequence elements can be incorporated into the expression vectors to facilitate integration of DNA into chromosomes, expression of the DNA and cloning of the vector. For example, the presence of enhancers upstream of the promoter or terminators downstream of the coding region can facilitate expression of the nucleic acid contained within the expression vector.

In order to express CSF5-hyaluronidase in prokaryotic or in yeast cells, the leader sequence (or secretory sequence) is typically removed. This can be done using standard techniques known by those skilled in the art. Once the desired CSF5-hyaluronidase cDNA clone is obtained, known and appropriate means are utilized to express the CSF protein, e.g. insertion into an appropriate vector, and transfection of the vector into an appropriate host cell, selection of transformed cells, and culture of these transformants to express CSF activity. Such methods are described in detail by Sambrook et al., *Molecular Cloning: a Laboratory Manual*, Cold Spring Harbor Laboratory Press, Cold Spring Harbor, N.Y., latest edition and by Ausubel et al., *Current Protocols in Molecular Biology*, latest edition. Suitable host cells include bacteria, e.g. *E. coli*, yeast mammalian e.g. CHO, and insect cells, e.g. Sf9 cells. The CSF5-hyaluronidase protein thus produced may have a methionine group at the N-terminus of the protein (herein called Met-CSF). The mature protein produced by prokaryotic and eukaryotic cells will be otherwise identical in amino acid sequence, but the eukaryotic product may be glycosylated to the same or a different extent as in the natural product. Various methods of obtaining CSF protein in accordance with the convention are illustrated in the Examples described below. Various cell transfection methods may be used, including electroporation, calcium phosphate precipitation, microinjection and cell fusion. Other methods or materials, e.g. vectors, will be readily apparent to those skilled in the art on the basis of the Examples and the foregoing description.

Pharmaceutically acceptable compositions of CSF5-hyaluronidase may be used to treat mammals suffering from monocytopenia, particularly those associated with radiation, chemotherapy, and viral infections. Monocytopenia is defined as an abnormal decrease in the proportion of monocytes in the blood. A variety of mammalian hosts may be treated according to the subject invention. Such hosts include rare or valuable mammals, pets and livestock, humans, and the like.

As discussed above, the subject methods result in the increase in cells of the monocytic lineage by administration of a recombinant protein of CSF5-hyaluronidase or nucleic acid encoding the same. CSF5-hyaluronidase may be used in combination with additional treatment modalities, including surgery, radiation therapy and chemotherapy. Methods of surgery for both biopsy and reduction or elimination of tumor mass are known to those of skill in the art. Radiation therapy is also known to those of skill in the art and includes electromagnetic radiation, e.g., high frequency x-rays, and subatomic particle radiation, e.g., alpha particles, beta particles, neutrons, protons, mesons, and heavy ions. Finally, a variety of chemotherapeutic agents and methods for their use in cancer therapy are known and include: alkylating agents, e.g., Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, LPAM), Busulfan (Myleran), Thiotepa (Triethylenethiophosphoramide), Carmustine (BiCNU, BCNU), Lomustine (CeeNU, CCNU), Streptozocin (Zanosar), and the like; plant alkaloids, e.g., Vincristine (Oncovin), Vinblastine (Velban, Velbe), Paclitaxel (Taxol), and the like; antimetabolites, e.g., Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA), and the like; antibiotics, e.g., Dactinomycin (Actinomycin D Cosmegen), Doxorubicin (Adriamycin), Daunorubicin (duanomycin, Cerubidine), Idarubicin (Idamycin), BJeomycin (Blenoxane), Picarnycin (Mithramycin, Mithracin), Mitomycin (Mutarnycin), and the like, and other anticellular proliferate agents, e.g., Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16213), Amsarcrine (AMSA, m-AMSA), Mitotane (Lysodren), Mitoxantrone (Novatrone), and the like.

In using the subject methods in combination with one or more of the above reviewed conventional treatment modalities, the timing of the different modalities may be controlled so as to obtain optimum results with regard to beneficial effects upon the cells of the monocytic lineage.

Pharmaceutically acceptable compositions contemplated for use in the practice of the present invention can be used in the form of a solid, a solution, an emulsion, a dispersion, a micelle, a liposome, and the like, wherein the resulting composition contains one or more of the active compounds contemplated for use herein, as active ingredients thereof, in admixture with an organic or inorganic carrier or excipient suitable for nasal, enteral or parenteral applications. The active ingredients may be compounded, for example, with the usual non-toxic, pharmaceutically or physiologically acceptable carriers for tablets, pellets, capsules, troches, lozenges, aqueous or oily suspensions, dispersible powders or granules, suppositories, solutions, emulsions, suspensions, hard or soft capsules, caplets or syrups or elixirs and any other form suitable for use. The carriers that can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents may be used. The active compounds contemplated for use herein are included in the pharmaceutical composition in an amount sufficient to produce the desired effect upon the target process, condition or disease.

In addition, such compositions may contain one or more agents selected from flavoring agents (such as peppermint, oil of wintergreen or cherry), coloring agents, preserving agents, and the like, in order to provide pharmaceutically elegant and palatable preparations. Tablets containing the active ingredients in admixture with non-toxic pharmaceutically acceptable excipients may also be manufactured by known methods. The excipients used may be, for example, (1) inert diluents, such as calcium carbonate, lactose, calcium phosphate, sodium phosphate, and the like; (2) granulating and disintegrating agents, such as corn starch, potato starch, alginic acid, and the like; (3) binding agents, such as gum tragacanth, corn starch, gelatin, acacia, and the like; and (4) lubricating agents, such as magnesium stearate, stearic acid, talc, and the like. The tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed. The tablets may also be coated by the techniques described in the U.S. Pat. Nos. 4,256,108; 4,160,452; and 4,265,874, to form osmotic therapeutic tablets for controlled release.

When formulations for oral use are in the form of hard gelatin capsules, the active ingredients may be mixed with an inert solid diluent, for example, calcium carbonate, calcium phosphate, kaolin, or the like. They may also be in the form of soft gelatin capsules wherein the active ingredients are mixed with water or an oil medium, for example, peanut oil, liquid paraffin, olive oil and the like.

Formulations may also be in the form of a sterile injectable suspension. Such a suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,4-butanediol. Sterile, fixed oils are conventionally employed as a solvent or suspending medium. For this purpose, any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Formulations contemplated for use in the practice of the present invention may also be administered in the form of suppositories for rectal administration of the active ingredients. These compositions may be prepared by mixing the active ingredients with a suitable non-irritating excipient, such as cocoa butter, synthetic glyceride esters of polyethylene glycols (which are solid at ordinary temperatures, but liquify and/or dissolve in the rectal cavity to release the active ingredients), and the like.

In addition, sustained release systems, including semi-permeable polymer matrices in the form of shaped articles (e.g., films or microcapsules) can also be used for the administration of the active compound employed herein. The CSF5-hyaluronidase can also be provided as a unit dosage such as a septum-sealed vial, either lyophilized or in aqueous solution.

The amount of CSF5-hyaluronidase administered to a patient will vary depending upon the condition to be treated, the severity of the condition, and the response of the patient to the treatment. In general, the amount of CSF5-hyaluronidase administered is between about 0.01 µg/kg and 1,000 mg/kg, preferably between about 0.1 µg/kg and 100 mg/kg, and more preferably between about 1 µg/kg and 10 mg/kg. Dosage optimization can be performed using standard dose-response curves.

EXAMPLE 1

Purification of Human Hyaluronidase-CSF5

To two liters of human plasma (Irwin Memorial Blood Bank, San Francisco, Calif.), 0.02% sodium azide, 50 mM NaCI, 5% sucrose and 7.5% Triton X-114 (Boehringer Mannheim, Indianapolis, Ind.) were dissolved at 4° C. with stirring for 90 min followed by centrifugation at 10,000×g for 30 min. The plasma was then subjected to temperature-induced phase extraction at 37° C. The extract was centrifuged at 10,000×g for 30 min at 37° C. to clarify the two phases. The detergent-rich phase was removed and diluted to 2 L with ice cold 50 mM (N-[2-hydroxyethyl]piperazine-N'-[2-ethanesulfonic acid]) (HEPES), pH 7.5, 0.15 M NaCI, followed by repartitioning at 37° C. with centrifugation. This washing procedure was repeated three times. The final detergent phase was diluted sixfold with 25 mM (2-[N-Morpholino]ethanesulfonic acid) (MES), pH 6.0, and 20 mL of equilibrated SP SEPHAROSE cation exchange resin was added (Pharmacia, Piscataway N.J.) and stirred overnight at 4° C. The beads were collected by centrifugation and washed with 25 mM MES, pH 6.0, containing 46 mM octylglucoside (Boehringer Mannheim). CSF5-Hyaluronidase was eluted from the beads by the addition of 0.3 M NaCI in MES buffer pH 6.0 with several washes. The SP SEPHAROSE eluant was concentrated by ultrafiltration using a YM3 membrane (Amicon, Beverly, Mass.) and desalted into 10 mM P04 pH 7.4 with 25 mM NaCI, 46 mM octylglucoside on a FPLC Fast-Desalting column (Pharmacia). The hyaluronidase preparation was then combined with 10 mL of hydroxyapatite resin (Biorad, Richmond, Calif.) equilibrated in the same buffer, and left on a rocker overnight at 4° C. CSF5-hyaluronidase did not adsorb to the resin and was recovered in the supernatant. The supernatant was then concentrated to 0.5 mL on a CENTRIPLUS YM3 concentrator (Amicon, Beverly, Mass.), and applied to a 12.5% polyacrylamide gel on a PHASTGEL electrophoresis system (Pharmacia), then silver-stained according to the manufacturer's instructions to ensure purity. Protein determinations were measured throughout the purification using the Lowry (Pierce, Rockford, Ill.) or Bradford (Biorad) assays with BSA as a standard.

CSF5-Hyaluronidase partitioned into the temperature-induced Triton X-114 detergent phase and gave a 60-fold enrichment. The activity was very stable at 37° C. in the presence of non-ionic detergents. Removal of Triton X-114 was performed by batch absorption onto a SP SEPHAROSE cation exchanger resin. The post SP SEPHAROSE preparation could be purified to homogeneity as determined by silver staining. Batch adsorption using hydroxyapatite resin, resulted in an overall, purification of 1.5-million fold. The specific activity of the enzyme activity of the CSF5-hyaluronidase (100,000 rTRU/mg) was approximately equivalent that of the reported values for the sperm hyaluronidase, PH-20 (Harrison, *Biochem. J.* 252:865-874, 1988), thereby ruling out contamination of the enzyme factor with a minor colony stimulating factor contaminant. The protein migrated on SDSPAGE with a relative molecular mass of 57 kDa.

EXAMPLE 2

Generation of Anti-Csf5-Hyaluronidase Monoclonal Antibodies

Six week-old female BALB/c mice were immunized using purified antigen from the post hydroxyapatite step described in Example 1 using established procedures (Harlow, *Antibodies: a Laboratory Manual*, Cold Spring Harbor Laboratory Press, Cold Spring Harbor, N.Y., 1988). Hybridomas were obtained by fusion of spleen cells and myeloma cells using standard Ed Harlow, D. L. *Antibodies: a laboratory manual* Cold Spring Harbor Laboratory, Cold Spring Harbor, N.Y. 1988). Hybridomas secreting anti-CSF5-hyaluronidase antibodies were screened by a modified enzyme capture assay. The bHA (Frost et al. 1997a *Anal Biochem.* 251:263-9.) enzyme substrate was coated onto COVALINK plates (Placerville, N.J.) under the same conditions as those described for the microtiter based enzyme assay (Frost et. al 1997a) except that 1.25/µg/well of goat anti-mouse IgG (Jackson Immunolabs, West Grove, Pa.) was included with the bHA so that both bHA and goat anti-mouse IgG were covalently coupled to the plates. Hybridoma supernatants were incubated with diluted human plasma for 60 mm at 37° C. followed by incubation in the bHA/antimouse-IgG plates for 60 mm at 37° C. Plates were washed 5 times with PBS containing 1% Triton X-100, and 10 mg/ml BSA followed by the addition of formate assay buffer and incubation at 37° C. for 60 min. Digested bHA as a result of immunoprecipitated CSF5-hyaluronidase was detected as in the standard assay.

An enzyme capture assay was developed for screening hybridomas that exploited the lack of activity of CSF5-hyaluronidase at neutral pH and the fact that the protein had no binding affinity for HA above pH 4.5, as determined by HA-SEPHAROSE affinity chromatography. The hybridoma supernatants were incubated with crude plasma at neutral pH in the bHA/anti-mouse IgG microtiter plates to immunoprecipitate the antibody-antigen complex. Eight clones were identified from twenty hybridoma fusion plates using this screening procedure. One clone of the IgG2a class, 17E9, was used to generate ascites. Addition of serial dilutions of the 17E9 antibody to human plasma followed by immunoprecipitation with Protein-A resulted in precipitation of all detectable acid-active hyaluronidase activity.

EXAMPLE 3

Immunoprecipitation and Immunoaffinity Purifications

Purified IgG2a from the 17E9 anti-CSF5-hyaluronidase hybridoma clone prepared as described in Example 2 was used for routine immunoprecipitation and purifications. For the immunoprecipitation of CSF5-hyaluronidase from plasma, serial dilutions of purified 17E9 IgG or control mouse IgG2a were mixed with plasma diluted in RIPA buffer (1% NP40,1% deoxycholate, 1% Triton X-100, 5 mM EDTA in PBS), followed by immunoprecipitation with protein-A beads. Residual CSF5-hyaluronidase activity in the supernatant was then measured in the microtiter assay. For the immunoaffinity purification of CSF5-hyaluronidase, 3 mg of purified IgG from the 17E9 hybridoma clone was coupled to a 1 mL HITRAP NHS-activated column (Pharmacia). Plasma or HEK-293 human embryonic kidney cell recombinant CSF5-hyaluronidase conditioned media was diluted 1:2 with RIPA buffer, and passed over the anti-CSF5-hyaluronidase IgG column. The column was first washed with PBS containing 2M NaCl, 100 mM octylglucoside followed by washing with 100 mM citrate pH 4.0, 0.15M NaCl and octylglucoside, and then eluted with the same buffer adjusted to pH 3.0.

Hyaluronidase could be purified to homogeneity in a single step from human plasma by immunoaffinity chromatography using the 17E9 antibodies. After washing the column under stringent conditions, the enzyme eluted at pH 4.0 and was purified to homogeneity as determined by SDS-PAGE and amino acid sequencing. Three sequences were obtained from CNBr digests of immunopurified protein.

EXAMPLE 4

Amino Acid Sequencing of CSF5-Hyaluronidase

For N-terminal amino acid sequencing, the immunoaffinity purified protein was electroblotted from an SDS gel to a PVDF membrane (ABI, Foster City, Calif.) and sequenced by Edman degradation. Internal peptides of immunoaffinity purified CSF5-hyaluronidase were obtained through digestion with cyanogen bromide (CNBr) followed by fragment separation on an HPLC (Vydac C-18) column.

The nucleotide and amino acid sequences of CSF5-hyaluronidase are shown in SEQ ID NOS: 8 and 9, respectively. The N-terminal and internal amino acid sequences of CSF5-hyaluronidase are 100% identical to the conceptual translation of the cDNA. Alignment (Frohman et al., *Proc. Natl. Acad. Sci. U.S.A.* 85:8998-9002, 1988)) of the predicted translation of colony stimulating factor and human PH-20 indicated 40% sequence identity and 60% homology at the amino acid level. PH-20 is a sperm specific neutral-active hyaluronidase. The homology between a strictly acid-active hyaluronidase and PH-20 suggests that all mammalian β,1-4 hyaluronidases may be members of a conserved family.

EXAMPLE 5

CSF5-Hyaluronidase cDNA Cloning

A TBLASTN (Altschul et al., *J. Mol. Bid.* 215:403-410, 1990) homology search (compares a protein sequence against a nucleotide sequence database translated in all reading frames) of the Expressed Sequence Tag (EST) database (Lennon et al., *Genomics* 33:151-152, 1996) revealed an I.M.A.G.E. Consortium clone (Lennon et al., supra.) (GenBank Accession No. AA223264) which was 100% identical to the N-terminal amino acid sequence of determined in accordance with Example 4. This EST is available from Genome Systems (St. Louis, Mo.) and is 2 kb including the poly-A tail at the 3' end. To obtain the 5' end of the cDNA, 5' RACE (Boguski et al., *Nature Genetics* 4:332.333, 1993) was performed on a Marathon Ready™ human heart cDNA library (Clontech Laboratories, Inc., Palo Alto, Calif.) according to the manufacturer's instructions, with some modifications. Briefly, for the first PCR reaction, the following primers were used: HPHRACE1 (5-ATCGAAGACACT-GACATCCACGTCCACACC-3') (SEQ ID NO: 1) and the Adapter Primer 2 (AP2) from Clontech (5'-ACTCACTAT-AGGGCTCGAGCGGC-3') (SEQ ID NO: 2); annealing/extension was at 73° C. for 40 cycles. Advantage™ KlenTaq polymerase mix (Clontech) was used to provide a "hot start". A diffuse band of 800 bp was observed on agarose gel electrophoresis. The band was excised using a QIAQUICK gel extraction kit (Qiagen Inc. Chatsworth, Calif.) according to the manufacturer's instructions. The excised DNA was used as a template for a second nested PCR using primer HPHRACE2 (5'-TGCCTCTCCAGGCACCACTGGGT-GTTTGC-3') (SEQ ID NO: 3) with the AP2 primer (SEQ ID NO: 2); annealing/extension was at 72° C. for 15 cycles. A "hot start" was employed as described above. A single sharp band of 800 bp was observed on agarose gel electrophoresis. 120 ng of the PCR product was ligated into the TA cloning vector pCR2.1 (Invitrogen, San Diego, Calif.) and used to transform ONE SHOT TOP 10F' competent cells according to the manufacturer's instructions. Positive colonies were sequenced as above. The 800 bp product exhibited 100% overlap with the 5' end of the EST by 300 bp.

For generation of the CSF5-hyaluronidase cDNA coding sequence, a PCR reaction was performed using the EST as template with the following primers: HPHF15'-GTGC-CATGGCAGCCCACC-3' (SEQ ID NO: 4) and HPHR15'-ATCACCACATGCTCTTCCGC-3' (SEQ ID NO: 5) with annealing at 58° C. for 35 cycles. 120 ng of the PCR product was cloned into the TA expression vector pCR3.1-Uni (Invitrogen, San Diego, Calif.) and used to transform One Shot T0P10F' competent cells according to the manufacturer's instructions. Colony stimulating factor in the pCR3.1-Uni expression vector was purified from positive colonies and verified by restriction mapping with Pst I and Dra III. The insert was sequenced by standard methods and found to contain a complete open reading frame which was 100% identical to the HYAL1 gene (SEQ ID NO: 8) described in (Frost et al 1997) and in GenBank Accession No. U03056 (Wei et al., 1996).

EXAMPLE 6

Expression of Recombinant CSF5-Hyaluronidase 1N Human Embryonic Kidney Cells

To substantiate the identity of colony stimulating factor with the cloned gene, the cDNA was stably transfected into human embryonic kidney (HEK-293) cells. The cDNA was amplified from the EST and then subcloned into a unidirectional expression vector. This vector was used to generate HEK-293 clones overexpressing hyaluronidase activity.

The CSF5-hyaluronidase-containing vector was transfected into 75% confluent T75 flasks of human embryonic kidney (HEK-293) cells for five hours in the absence of serum using 9 µg of purified plasmid and 60 µof LIPOFECTIN transfection reagent (Gibco BRL) in 20 mL of DME/F12 50/50. The transfected cells were then grown for an additional 48 h in DME/F12 50/50 mix containing 10% fetal bovine serum (FBS). After 48 h, cells were plated by limited dilution into 24 well plates in the presence 500 µg/ml G418 to select for neomycin resistance. After 14 days, the conditioned media of resistant colonies was assayed for hyaluronidase activity using the protocol described herein. Colonies with high level expression were then expanded. For the analysis of the recombinant CSF5-hyaluronidase and comparison with the biochemically purified protein, a recombinant overexpressing hyaluronidase HEK 293 cell line was grown for 48 h in serum free medium, and the conditioned medium was passed over a 17E9 anti-CSF immunoaffinity column. Recombinant enzyme eluted using the same protocol as for human plasma. Purified recombinant hyaluronidase was then blotted to PVDF and subjected to N-terminal amino acid sequencing to ensure authenticity.

The parental HEK 293 cell line produced undetectable levels of hyaluronidase in the conditioned media and cell layer whereas the stably transfected clones secreted approximately 15 rTRU/ml, a 3,000 fold increase. To ensure that the hyaluronidase activity found in the recombinant HEK-293 cell clones was the product of the transfected cDNA, the hyaluronidase was immunoaffinity purified from serum free conditioned medium of the HEK-293 overexpressing clone and sequenced the eluent from the 17E9 column. This yielded the same processed N-terminus (FRGPLLP) (SEQ ID NO:10) found in human plasma and a migrated as a single band on SDSPAGE. This band aligned with the purified plasma using both silver stain and substrate gel zymography. A commercial preparation of testicular hyaluronidase (3,000 TRU/mg solid) was run for comparison of the specific activity. The pH activity curve of recombinant colony stimulating factor has the same profile as the immunoaffinity-purified plasma enzyme, with no activity in vitro above pH 4.5, in contrast to bovine testicular hyaluronidase, which has maximal activity above pH 7.

EXAMPLE 7

Organ Survey of CSF5-Hyaluronidase Transcripts

Nested PCR primers amplifying the 1.3 kb coding region of the colony stimulating factor cDNA were used to analyze the tissue distribution of transcripts in λgt10 cDNA libraries. For the first round of PCR the following primers were used: HPHF2 (5'-AGGTTGTCCTCGACCAGTC-3') (SEQ ID NO: 6) and HPHR2 (5'ATGTGCAACTCAGTGTGTGGC-3') (SEQ ID NO: 7) at an annealing temperature of 58"C. The second PCR reaction consisted of 15 cycles at an annealing temperature of 58° C. with primers HPHF1 and HPHR1 (see above). PCR products were found in heart, kidney, liver, lung, placenta, and skeletal muscle, but were not detected in brain.

EXAMPLE 8

Stimulation of Monocyte Colony Formation by CSF5-Hyaluronidase

Colony stimulating activity of CSF5-hyaluronidase was determined in serum free culture using recombinant CSF5-hyaluronidase supernatant from HEK293 cells. Briefly, whole blood from normal donors was collected in EDTA. Blood was diluted 1:2 in phosphate buffered saline (PBS) and overlayed in a 2:1 ratio onto Lymphoprep. Samples were centrifuged at 1,500×g for 20 min and the lymphocyte band was removed. Cells were washed twice with serum-free Dulbecco's Modified Eagle Medium (DMEM) and plated serum free in 24 well dishes in DMEM for 1 hour at 37° C. Plates were then washed twice with serum free DMEM, and remaining adherent peripheral blood mononuclear cells were used for colony forming assays.

In order to determine the colony forming activity of CSF5-hyaluronidase, HEK293 cells overexpressing CSF5-hyaluronidase as described in Example 6 were grown serum free in HEK293SFM medium (Gibco BRL) for six days with an innoculum of $1\times10^5$ cells/ml. As a control, HEK293 cells not expressing CSF5-were grown under identical conditions with the same innoculum for six days. The amount of CSF5-hyaluronidase activity present in the media after six days was determined by an enzyme based assay based upon an approximate specific activity of 100,000 TRU/mg protein (Frost et al. 1997a). The results are shown in Table 3. The half maximal stimulation of monocyte colony formation occurred at about 5 ng/ml hyaluronidase.

| Concentration of HYAL1 (ng/ml) via specific activity | Monocyte Colony Formation % of FBS | Control HEK Media Dilutions | Monocyte Colony Formation |
|---|---|---|---|
| 100 ng (10 TRU/ml) | ++++ | 1:1 (OTRU/ml) | 0 |
| 50 ng/ml (5 TRU/ml) | ++++ | 1:2 (OTRU/ml) | 0 |
| 25 (2.5 TRU/ml) | ++++ | 1:4 (OTRU/ml) | 0 |
| 12.5 (1.25 TRU/ml) | ++ | 1:8 (OTRU/ml) | 0 |
| 6.26 (0.625 TRU/ml) | + | 1:16 (OTRU/ml) | 0 |
| 1 ng/ml (0.1 TRU/ml) | 0 | 1:32 (OTRU/ml) | 0 |

CSF5-hyaluronidase media or corresponding control media from HEK control cells was applied in serial dilutions in HEK293SFM to adherent peripheral blood mononuclear cells (PBMC). Cells were cultured in diluted CSF5-hyaluronidase for ten days. Cellular proliferation was observed at day 10 by fixation of cells in methanol containing 1% crystal violet and observed under an inverted Leitz microscope. Resultant colonies were determined to be of monocytic morphology by nuclear staining with Giemsa.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit and scope of that which is described and claimed.

What is claimed is:

1. An in vitro method for increasing the number of myeloid progenitors in a cell population, comprising the step of contacting in vitro a cell population comprising myeloid progenitors with an exogenously-derived colony-stimulating factor 5 hyaluronidase (CSF5hyaluronidase), thereby increasing the number of myeloid progenitors in the cell population.

2. The method of claim 1, wherein the cell population is from a mammal with a myelosuppressed condition.

3. The method of claim 1, wherein the myeloid progenitor cells are for therapeutic use.

* * * * *